United States Patent [19]

Sze

[11] 4,284,781
[45] Aug. 18, 1981

[54] SUPPORTED VANADIA CATALYST AND USE THEREOF FOR NITRILE PRODUCTION

[75] Inventor: Morgan C. Sze, Upper Montclair, N.J.

[73] Assignee: The Lummus Company, Bloomfield, N.J.

[21] Appl. No.: 882,667

[22] Filed: Mar. 2, 1978

Related U.S. Application Data

[60] Division of Ser. No. 819,771, Jul. 28, 1977, Pat. No. 4,092,271, which is a continuation-in-part of Ser. No. 727,060, Sep. 27, 1976, abandoned.

[51] Int. Cl.$^2$ .................. C07D 213/57; C07C 120/14
[52] U.S. Cl. ................................ 546/286; 260/465 C; 260/465 H; 546/176; 544/224; 544/242; 544/336; 260/347.7; 260/326.15; 260/326.62; 548/378; 548/146; 548/206; 548/214; 548/236; 548/240; 549/61
[58] Field of Search ............ 260/294.9, 465 C, 465 H; 546/286, 176; 544/224, 336, 242

[56] References Cited

U.S. PATENT DOCUMENTS

| | | | |
|---|---|---|---|
| 3,803,205 | 4/1974 | Shang et al. | 252/461 |
| 3,812,171 | 5/1974 | Neikam et al. | 252/461 |
| 3,959,337 | 5/1976 | Bushick et al. | 252/476 |

Primary Examiner—Alan L. Rotman
Attorney, Agent, or Firm—Louis E. Marn; Elliot M. Olstein

[57] ABSTRACT

Vanadia supported on a silica-alumina or gamma-alumina support in an amount to provide a vanadia to support weight ratio ranging from about 0.3:1 to about 3:1 substantially entirely within the pores of the support, the vanadia having been placed in molten form substantially within the pores of a support having a surface area greater than about 50 m$^2$ gram, a porosity greater than about 0.4 cc/gram which further includes an alkali metal, with the vanadium metal to alkali metal mole ratio being from 2:1 to 30:1. At least a portion of the alkali metal is preferably in the form of alkali metal vanadate. The catalyst is used for the production of nitriles from a compound containing at least one alkyl group.

24 Claims, No Drawings

SUPPORTED VANADIA CATALYST AND USE THEREOF FOR NITRILE PRODUCTION

This application is a division of U.S. Pat. application Ser. No. 819,771 filed on July 28, 1977, and now U.S. Pat. No. 4,092,271, with the aforesaid application being a continuation in part of U.S. Pat. application Ser. No. 727,060, filed on Sept. 27, 1976, and now abandoned.

This invention relates to a supported vanadia catalyst and the use thereof for the production of nitriles.

U.S. Pat. No. 3,963,645 discloses a supported vanadia catalyst wherein the vanadia is supported on a silica-alumina or gamma-alumina support in an amount to provide a metal oxide to support weight ratio ranging from about 0.3:1 to about 3:1 substantially entirely within the pores of the support, with the vanadia having been placed in molten form within the pores of the support which has a surface area greater than about 50 $m^2$/gram and a porosity greater than about 0.4 cc/gram. The supported vanadia catalyst is particularly suitable for the production of nitriles by oxidative ammonolysis (ammoxidation). The present invention is directed to an improvement in the supported vanadia catalyst of the aforesaid patent, and the use of such an improved catalyst for the production of nitriles.

In accordance with the present invention, there is provided a catalyst of vanadia supported on a porous support in an amount to provide a vanadia to support weight ratio ranging from about 0.3:1 to about 3:1 substantially entirely within the pores of the support, with the vanadia having been placed in molten form substantially within the pores of a support having a surface area greater than about 50 $m^2$/gram, a porosity greater than about 0.4 cc/gram, with the catalyst further containing an alkali metal in an amount to increase the catalytic effect of the catalyst.

More particularly, the catalyst includes an alkali metal which is either lithium, sodium, potassium, rubidium or cesium, in an amount to provide a vanadium metal to alkali metal mole ratio of from about 2:1 to 30:1, and preferably from about 8:1 to 20:1. The alkali metal is preferably sodium.

The support on which the vanadium pentoxide is to be supported has a surface area of greater than about 50 $m^2$/gram and a porosity greater than about 0.4 cc/gram. In general, the surface area of the support is no greater than about 600 $m^2$/gram and the porosity is no greater than about 1.2 cc/gram. Supports having a surface area of about 200 $m^2$/gram have been found to provide particularly good results. As representative examples of preferred supports having such properties there may be mentioned: silica-alumina, zeolites, alumina, including microcrystalline and the $\gamma$, $\delta$, $\eta$, $\kappa$ and $\chi$ modifications of alumina. The silica-alumina and gamma-alumina supports are particularly preferred.

The fused supported vanadia catalyst which is promoted with an alkali metal may be conveniently prepared by mixing the support with an aqueous solution of the alkali metal hydroxide to provide the desired amount of alkali metal in the support. The support containing the alkali metal is then mixed with vanadia and heated to above the fusion point of the vanadia to draw the vanadia into the pores of the alkali metal treated support.

As an alternative, the supported vanadia catalyst may be prepared by a fusion technique without initial treatment of the support with an alkali metal, followed by impregnation of the supported vanadia catalyst with an aqueous solution of the alkali metal hydroxide to provide the required amount of alkali metal, and heating to above the fusion point of vanadia.

As another alternative, the vanadia and an alkali metal compound such as the hydroxide or oxide, may be preblended in the appropriate amounts by procedures known in the art and the resulting blend supported on the support by the fusion technique.

The general technique for supporting the vanadium pentoxide within the pores of a porous support is described in U.S. Pat. No. 3,963,645.

In accordance with a preferred embodiment of the present invention, a particularly active form of the catalyst is produced by providing a mixture of alkali metal hydroxide and vanadia on the support and heating the supported mixture to the fusion temperature of the vanadia at a controlled heating rate. More particularly, the supported mixture is heated to the vanadia fusion temperature at an average rate of less than 20° F./minute, preferably less than 15° F./minute, with a particularly preferred heating rate being 10° F./minute or less. Thus, in general, the supported mixture is heated up to the fusion temperature over a time period of at least 1 hour, with particularly good results being achieved over a period of 2 hours or more.

The supported mixture is maintained at or above the fusion temperature for a time sufficient to place the vanadia substantially entirely within the pores of the support. In general, the supported mixture is maintained at a temperature of from 1300° F. to 1450° F. for a time period of from 1 to 10 hours.

In preparing the catalyst in accordance with the preferred procedure, i.e., controlled heating of vanadia and alkali metal hydroxide on the support, at least a portion of the alkali metal is present in the final catalyst as the alkali metal vanadate; preferably sodium vanadate. If the heating to fusion temperature is effected at a more rapid rate, alkali metal vanadate is not formed and such a catalyst has been found to be less selective for the production of nitriles, even though it is an improvement over the fused catalyst without the alkali metal. Thus, in accordance with the particularly preferred embodiment, the catalyst includes both vanadia and alkali metal vanadate, preferably sodium vanadate. In general, at least 10% by weight of the alkali metal is present as the vanadate.

The supported vanadia catalyst of the present invention is particularly suitable for the production of nitriles by oxidative ammonolysis (ammoxidation). The organic reactant employed as a starting material for the production of nitriles by ammoxidation is a compound including at least one alkyl group; namely, aromatic, aliphatic, alicyclic and heterocyclic compounds having at least one alkyl group.

As representative examples of alkyl substituted aromatic hydrocarbons which are suitable as starting materials, there may be mentioned the alkyl substituted benzenes and naphthalenes, and in particular, benzene which may contain two or more alkyl groups in which case the resulting product is a polynitrile. The alkyl group generally contains no more than 4 carbon atoms, preferably no more than 2 carbon atoms. As particular examples of suitable alkyl substituted aromatic hydrocarbons, there is: toluene; various xylenes to produce the various phthalonitriles; ethyl benzene, trimethyl benzenes, methylnaphthalenes, durene and the like.

As representative examples of suitable aliphatic compounds, there may be mentioned: olefinic hydrocarbons having at least one alkyl group, such as propylene and isobutylene to produce acrylonitrile and methacrylonitrile, respectively.

As representative examples of suitable alicyclic compounds, there may be mentioned: methylcyclopentane, methylcyclohexane, the alkyl substituted decalins, and the like.

The heterocyclic compounds useful as starting materials for producing nitriles by ammoxidation in accordance with the present invention include alkyl substituted furans, pyrroles, indoles, thiophenes, pyrazoles, imidazoles, thiazoles, oxazoles, pyrans, pyridines, quinolines, isoquinolines, pyrimidines, pyridazines, pyrazines and the like. The preferred heterocyclic compounds are the alkyl, preferably lower alkyl, substituted pyridines, with pyridines having an alkyl group in a beta-position with respect to the heterocyclic nitrogen atom being particularly preferred in that such pyridines can be converted to nicotinonitrile; in particular, 3-picoline, 2,3-and 2,5-dimethylpyridine, 2-methyl-5-ethylpyridine and 3-ethylpyridine.

The starting material, containing at least one alkyl group is converted to a nitrile by contacting the starting material with ammonia, in the vapor phase, in the presence of the supported vanadia catalyst of the present invention, either in the absence or presence of a free oxygen containing gas, preferably in the absence of a free oxygen containing gas. The contacting is generally effected at a temperature from about 300° C. to about 500° C., preferably from about 375° C. to about 475° C., with the contact time generally ranging from about 0.5 to about 15 seconds, preferably from about 2 to about 8 seconds. Reaction pressures generally range from about 1 to about 5 atmospheres. The mole ratio of ammonia to starting material generally ranges from about 2:1 to about 16:1, preferably from about 3:1 to about 8:1. If an oxygen-containing gas is employed in the feed, the gas is employed in an amount such that the quantity of oxygen and starting material in the feed is outside of the explosive range.

In accordance with the preferred embodiment of the invention, the starting material and ammonia are contacted with the supported vanadia catalyst of the present invention in the absence of oxygen, with the supported vanadia catalyst being periodically passed to another reactor (in general the supported vanadia catalyst is not maintained on stream for a period greater than about 30 minutes, preferably from about 2 to about 10 minutes), and contacted therein with a free oxygen containing gas to effect regeneration of the catalyst, generally at a time period from about 2 to about 20 minutes. The supported vanadia catalyst is then recycled to a nitrile production zone. It is believed that the supported vanadia catalyst is reduced during the nitrile production step and, consequently, periodic oxidation thereof is required to maintain the supported vanadia catalyst in the oxidized form necessary for the nitrile production.

The invention will be further described with respect to the following examples; however, it is to be understood that the scope of the invention is not to be limited thereby.

EXAMPLE I

Catalyst A (Present Invention)

3000 g. of silica-alumina fluid bed catalyst support (Grace 135) was slurried in 4500 g. of lwt. % NaOH and agitated for 30 minutes. After settling, the supernatent liquid was decanted and replaced with 4500 g. of water, and the mixture agitated for another 30 minutes. The mixture was again separated by decantation. After drying at 110° C., the treated support contained 0.9 wt. % Na. This support was then blended with 2000 g. of powdered vanadia and heated at 1400° F. for 5 hours in a slowly rotating cylindrical kiln. After cooling, the catalyst was removed from the kiln and screened through a 40 mesh screen.

Catlyst B 3000 g. of a silica-alumina fluid bed catalyst support (Grace 135) was blended with 2000 g. of powdered vanadia and heated at 1400° F. for 5 hours in a slowly rotating cylindrical kiln. After cooling, the catalyst was removed from the kiln and screened through a 40 mesh screen.

Catalysts A and B were then employed for the production of isophthalonitrile under the following conditions. The ammoxidation was effected in the absence of molecular oxygen with catalysts A and B being regenerated in a separate regenerator by contact with oxygen.

TABLE I

| Catalyst Type | B | A |
|---|---|---|
| Reactor Pressure, PSIG | 10 | 10 |
| Reactor Temp., °F. | 800 | 800 |
| Regenerator Temp., °F. | 910–930 | 910–930 |
| Catalyst circulation, gms/min. | 56 | 53 |
| Organic Feed Rate/cc/min. | 3.3 | 3.4 |
| Feed Composition | | |
| m-xylene, wt. % | 69 | 69 |
| M-toluonitrile, wt. % | 31 | 31 |
| NH₃ In feed | | |
| mol/mol. organic feed | 9.1 | 8.8 |
| Inert gas in feed | | |
| mol/mol. organic feed | 9.4 | 8.9 |
| Conversion, mol % | 52.5 | 41.5 |
| Ultimate Yield of Isophthalonitrile | | |
| Basis m-xylene, mol % | 80.7 | 86.6 |
| Basis ammonia, mol % | 27 | 40 |

Improved results are obtained by using the catalyst of the present invention (Catalyst A) as evidenced by increased ammonia and hydrocarbon yield.

EXAMPLE II

Catalyst A (Present Invention)

3000 g. of a silica-alumina fluid bed catalyst support (Grace 135) was slurried in 4500 g. of lwt. % NaOH and agitated for 30 minutes. After settling, the supernatent liquid was decanted and replaced with 4500 g. of water, and the mixture agitated for another 30 minutes. The mixture was again separated by decantation. After drying at 110° C., the treated support contained 0.9 wt. % Na. This support was then blended with 2000 g. of powdered vanadia and heated at the rate of 10° F./minute in a slowly rotating cylindrical kiln to a temperature of 1400° F. and maintained at such temperature for 5 hours. After cooling, the catalyst was removed from the kiln and screened through a 40 mesh screen.

In Runs A & B, the catalyst is employed for production of terephthalonitrile from p-xylene, and nicotinonitrile from beta-picoline, respectively. The ammoxidation was effected in the absence of molecular oxygen, with catalysts being regenerated in a separate regenerator by contact with oxygen.

TABLE II

|  | A | B |
|---|---|---|
| Reactor Pressure, PSIG | 25.0 | 15.0 |
| Reactor Temp., °F. | 800 | 775 |
| Regenerator Temp., °F. | 935-955 | 935-955 |
| Catalyst circulation, gms/min. | 112.8 | 73.8 |
| Organic Feed Rate, cc/min. | 6.7 | 8.0 |
| $NH_3$ in feed mol/mol. organic feed | 7.8 | 5.0 |
| Inert gas in feed mol/mol. organic feed | 0.7 | 0.6 |
| Conversion, mol % | 50.67 | 30.05 |

In Run A the following selectivities and yields are achieved:

| | | |
|---|---|---|
| | Terephthalonitrile | 93.53 |
| | p-tolunitrile | 0.00 |
| | benzonitrile | 0.04 |
| | carbon oxides | 6.43 |
| | Yields, mole % | |
| | Ultimate Organic | 93.53 |
| | Ammonia | 65.71 |

In Run B, the following selectivities and yields are achieved:

| | | |
|---|---|---|
| | Selectivity, mole % | |
| | Nicotinonitrile | 89.66 |
| | Pyridine | 0.74 |
| | Carbon Oxides | 9.60 |
| | Yields, mole % | |
| | Ultimate Organic | 89.66 |
| | Ammonia | 66.70 |

EXAMPLE III

Two catalysts are prepared as described with reference to Example II, (40% vanadia and 1% sodium) except that one catalyst was heated at the rate of 10° F./min. and the second at a rate of greater than 20° F./min.

In Runs A and B of Table III the catalysts are employed for producing isophthalonitrile from m-xylene. The ammoxidation is effected in the absence of molecular oxygen, and regeneration of the catalyst is effected on a cyclic basis rather than by continuous circulation of the catalyst, as in the previous examples.

TABLE III

| Run | A | B |
|---|---|---|
| Heating Rate for catalyst, °F./min. | >20 | 10 |
| Temperature, °F. | 800 | 800 |
| Catalyst Charge, g | 400 | 400 |
| Cat./OH, g/cc | 20.8 | 20 |
| Pressure, psig | 5 | 5 |
| GHSV (STP), $h^{-1}$ | 1040 | 1242 |
| $NH_3$/Organic, mol/mol | 5.4 | 6 |
| Selectivites, mol % | | |
| IPN | 56.5 | 64.9 |
| m-TN | 33.9 | 22.3 |
| BN | — | 1.7 |
| $CO_x$ | 9.5 | 11.1 |
| Conversion, % | 37.2 | 47.4 |
| Ultimate Yield, % | 85.4 | 83.8 |
| Space-Time Yield, g/gh | 0.15 | 0.20 |

The catalyst produced by slow heating provides improved selectivity in terms of conversion of methyl group to nitrile.

The present invention is an improvement over the catalyst of U.S. Pat. No. 3,963,645 in that the catalyst of the present invention, when employed for the production of nitriles, provides improved hydrocarbon selectivity and ammonia yield. Although Applicant does not intend to be limited by theoretical reasoning, it is believed that the improved catalytic effect results from a modification of the vanadia by reaction with the alkali metal at the fusion temperature.

Numerous modifications and variations of the present invention are possible in light of the above teachings and, therefore, within the scope of the appended claims, the invention may be practiced otherwise than as particularly described.

What is claimed is:

1. In a process for producing a nitrile by the catalytic ammoxidation of a compound containing at least one alkyl group convertible to a nitrile group by reaction with ammonia in the presence or absence of gaseous oxygen, the improvement comprising:
   effecting said ammoxidation with a catalyst comprising vanadia supported on a porous support in an amount to provide a vanadia to support weight ratio ranging from about 0.3:1 to about 3:1 substantially entirely within the pores of the support, said vanadia having been placed in molten form substantially within the pores of a support having a surface area greater than about 50 $m^2$ per gram, a porosity greater than about 0.4 cc per gram, said catalyst containing an alkali metal in an amount to provide a vanadia metal to alkali metal mole ratio of from 2:1 to 30:1.

2. The process of claim 1 wherein the support is silica-alumina.

3. The process of claim 2 wherein the alkali metal is sodium.

4. The process of claim 3 wherein the vanadia metal to alkali metal mole ratio is from about 8:1 to 20:1.

5. The process of claim 1 wherein the support is gamma-alumina.

6. The process of claim 5 wherein the alkali metal is sodium.

7. The process of claim 6 wherein the vanadia metal to alkali metal mole ratio is from about 8:1 to 20:1.

8. The process of claim 1 wherein a portion of the alkali metal is present as alkali metal vanadate.

9. The process of claim 8 wherein the support is silica-alumina.

10. The process of claim 9 wherein the alkali metal is sodium.

11. The process of claim 10 wherein the vanadia metal to alkali metal mole ratio is from about 8:1 to 20:1.

12. The process of claim 8 wherein the support is gamma-alumina.

13. The process of claim 12 wherein the alkali metal is sodium.

14. The process of claim 13 wherein the vanadia metal to alkali metal mole ratio is from about 8:1 to 20:1.

15. The process of claim 1 wherein the compound is benzene substituted with at least one alkyl group.

16. The process of claim 1 wherein the compound is a pyridine substituted with at least one alkyl group.

17. In a process for producing a nitrile by the catalytic ammoxidation of a compound containing at least one alkyl group convertible to a nitrile group by reaction with ammonia in the presence or absence of gaseous oxygen, the improvement comprising:

effecting said ammoxidation with a catalyst produced by heating a mixture of an alkali metal hydroxide and vanadia supported on a porous support having a surface area greater than about 50 meters square per gram and a porosity greater than about 0.4 cc per gram to the fusion temperature of vanadia at an average rate of less than 20° F. per minute, said vanadia and alkali metal hydroxide being employed in an amount to provide a vanadia to support weight ratio of from 0.3:1 to 3:1 substantially within the pores of the support and a vanadia metal to alkali metal mole ratio of from about 2:1 to 30:1, and maintaining the support mixture at vanadia fusion temperature to place the vanadia substantially entirely within the pores of the support.

18. The process of claim 17 wherein the support is selected from the group consisting of gamma-alumina and silica-alumina.

19. The process of claim 18 wherein the support is silica-alumina.

20. The process of claim 18 wherein the support is gamma-alumina.

21. The process of claim 18 wherein the compound is benzene substituted with at least alkyl group.

22. The process of claim 18 wherein the compound is a pyridine substituted with at least one alkyl group.

23. The process of claim 15 wherein the support is selected from the group consisting of gamma-alumina and silica-alumina.

24. The process of claim 16 wherein the support is selected from the group consisting of gamma-alumina and silica-alumina.

* * * * *